US009328953B2

(12) United States Patent
Eom et al.

(10) Patent No.: US 9,328,953 B2
(45) Date of Patent: May 3, 2016

(54) REFRIGERATOR AND CONTROLLING METHOD THEREOF

(75) Inventors: Yonghwan Eom, Seoul (KR); Hoyoun Lee, Seoul (KR); Youngjin Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 792 days.

(21) Appl. No.: 13/580,417

(22) PCT Filed: Feb. 17, 2011

(86) PCT No.: PCT/KR2011/001046
§ 371 (c)(1),
(2), (4) Date: Oct. 31, 2012

(87) PCT Pub. No.: WO2011/105717
PCT Pub. Date: Sep. 1, 2011

(65) Prior Publication Data
US 2013/0042638 A1 Feb. 21, 2013

(30) Foreign Application Priority Data

Feb. 23, 2010 (KR) .................. 10-2010-0016028
Feb. 23, 2010 (KR) .................. 10-2010-0016030

(51) Int. Cl.
*F25D 21/02* (2006.01)
*G01N 29/48* (2006.01)
*F25D 21/00* (2006.01)

(52) U.S. Cl.
CPC .............. *F25D 21/02* (2013.01); *G01N 29/48* (2013.01); *F25D 21/006* (2013.01); *F25D 2700/02* (2013.01); *G01N 2291/015* (2013.01); *G01N 2291/0251* (2013.01); *G01N 2291/102* (2013.01)

(58) Field of Classification Search
CPC .......... F25D 21/02; F25D 21/08; F25D 21/06
See application file for complete search history.

(56) References Cited

U.S. PATENT DOCUMENTS 2,200,801 A * 5/1940 Money ............................. 62/128
3,280,577 A * 10/1966 Kobayashi et al. ............. 62/126
(Continued)

FOREIGN PATENT DOCUMENTS

| JP | 50-043943 U | 5/1975 |
| JP | 2000-320948 A | 11/2000 |
| JP | 2008-232605 A | 10/2008 |

*Primary Examiner* — Ljiljana Ciric
*Assistant Examiner* — Alexis Cox
(74) *Attorney, Agent, or Firm* — Birch, Stewart, Kolasch & Birch, LLP

(57) ABSTRACT

A refrigerator includes a compressor, a condenser, an expansion unit, an evaporator for evaporating a refrigerant that has passed through the expansion unit, a heating unit for providing heat for defrosting the evaporator, a photographing device provided at one side of the evaporator and disposed to photograph the evaporator, so as to sense the amount of frost on the evaporator, the photographing device including a photographing unit for photographing frost on the evaporator and the surrounding background, and a control unit configured to determine the amount of frost on the evaporator from an image taken by the photographing device by acquiring pixel values which are proportionate to the amount of frost on the evaporator by applying image processing which includes binarization that separates the frost from other acquired images to determine the amount of frost on the evaporator, the control unit further configured to control the heating unit to operate when the amount of frost exceeds a predetermined amount.

7 Claims, 15 Drawing Sheets

(56) References Cited

U.S. PATENT DOCUMENTS

| | | | |
|---|---|---|---|
| 3,822,560 A * | 7/1974 | Hansen et al. | 62/140 |
| 4,045,971 A * | 9/1977 | Brenner, Jr. | 62/140 |
| 4,347,709 A * | 9/1982 | Wu et al. | 62/140 |
| 4,450,691 A * | 5/1984 | Taylor | 62/140 |
| 4,663,941 A * | 5/1987 | Janke | 62/156 |
| 4,860,551 A * | 8/1989 | Query | 62/140 |
| 6,144,022 A * | 11/2000 | Tenenbaum et al. | 250/208.1 |
| 6,207,967 B1 * | 3/2001 | Hochstein | 250/574 |
| 6,429,933 B1 * | 8/2002 | Jackson, Jr. | 356/239.8 |
| 8,477,192 B2 * | 7/2013 | Capello | G01N 21/359 340/932 |
| 9,032,745 B2 * | 5/2015 | Ashrafzadeh | F25C 5/187 62/135 |
| 2005/0120727 A1 * | 6/2005 | Flinner et al. | 62/126 |
| 2005/0189493 A1 * | 9/2005 | Bagley et al. | 250/341.8 |
| 2005/0257558 A1 * | 11/2005 | Yoshioka et al. | 62/324.5 |
| 2006/0157462 A1 * | 7/2006 | Weiss et al. | 219/203 |
| 2009/0235679 A1 * | 9/2009 | Bagley | 62/140 |
| 2010/0229575 A1 * | 9/2010 | Shaw | 62/81 |
| 2013/0081415 A1 * | 4/2013 | Kim et al. | 62/129 |
| 2013/0081416 A1 * | 4/2013 | Kim et al. | 62/151 |
| 2014/0070698 A1 * | 3/2014 | Pierce et al. | 315/82 |
| 2014/0182318 A1 * | 7/2014 | Eom et al. | 62/129 |

* cited by examiner

REFRIGERATOR AND CONTROLLING METHOD THEREOF

BACKGROUND OF THE INVENTION

1. Field of the Invention

The present invention relates to a refrigerator and a controlling method thereof.

2. Description of the Related Art

In general, refrigerators are apparatuses that can keep food fresh for a predetermined period by cooling a storage chamber, that is, a freezing compartment or a cool chamber while repeating a refrigeration cycle. The refrigeration cycle includes a compressor, a condenser, an expansion unit, and an evaporator.

The refrigerators include a main body that forms storage spaces and doors that selectively close the main body. Reserves are received in the storage spaces and a user can open the doors to take out the reserves.

Meanwhile, the evaporator is a heat exchanger that supplies cold air to the freezing compartment or the cool chamber. When the evaporator is used for a long period of time, wet air freezes and frosts over the outer side of the evaporator.

According to the refrigerators of the related art, there is a problem in that heat exchange efficiency of the evaporator is reduced by the frost on the surface of the evaporator, and accordingly, the cold air cannot easily supplied to the storage chamber.

SUMMARY OF THE INVENTION

The present invention has been made in an effort to provide a refrigerator in which an evaporator with frost can be effectively defrosted.

Further, the present invention provides a refrigerator that can sense the amount of frost on an evaporator by using soundsource transmitting and receiving units.

Further, the present invention provides a refrigerator that can sense the amount of frost on an evaporator by using a photographing device.

An aspect of the present invention provides a refrigerator including: a compressor, a condenser, and an expansion unit that constitute a refrigeration cycle; an evaporator that evaporates a refrigerant that has has passed through the expansion unit; a heating unit that provides heat for defrosting the evaporator; and a frost sensor unit that is provided at one side of the evaporator to sense the amount of frost on the evaporator, in which the operation of the frost sensor unit starts on the basis of whether operation conditions of the frost sensor unit are recognized and the heating unit selectively generates heat in accordance with the sensing result of the frost sensor unit.

Another aspect of the present invention provides a refrigerator including: a storage chamber where reserves are cooled and stored; an evaporator that supplies cold air to the storage chamber; a defrosting heater that removes frost generate on the surface of the evaporator; a transmitting unit that is provided at one side of the evaporator and transmits a sound wave or an ultrasonic signal of a predetermined magnitude; a receiving unit that receives a signal of a magnitude smaller than that of the sound wave or the ultrasonic signal; and a control unit that controls the defrosting heater to operate, when the magnitude of the signal received by the receiving unit is smaller than a predetermined value.

Another aspect of the present invention provides a refrigerator including: a storage chamber where reserves are stored; an evaporator that expands a refrigerant to supply cold air to the storage chamber; a heating unit that defrosts the evaporator; a photographing unit that is provided at one side of the evaporator and operates to take a picture of the evaporator and the portion around the evaporator; and a control unit that determines the amount of frost on the evaporator by separating the image of the evaporator and the image of the portion around the evaporator from the image taken by the photographing.

Another aspect of the present invention provides a method of controlling a refrigerator, which includes: exchanging heat in an evaporator, when a refrigeration cycle is performed; operating a frost sensor unit that senses the amount of frost on the evaporator, when a predetermined condition is satisfied; recognizing the amount of frost on the evaporator; and determining operation of a heating unit on the basis of whether the amount of frost is a predetermined value or more.

DETAILED DESCRIPTION OF THE PREFERRED EMBODIMENTS

Detailed exemplary embodiments of the present invention will be described hereafter with reference to the drawings. However, the spirit of the present invention is not limited to the exemplary embodiments and other exemplary embodiments may be proposed by those understanding the spirit of the present invention without departing from the spirit.

Figure 1:
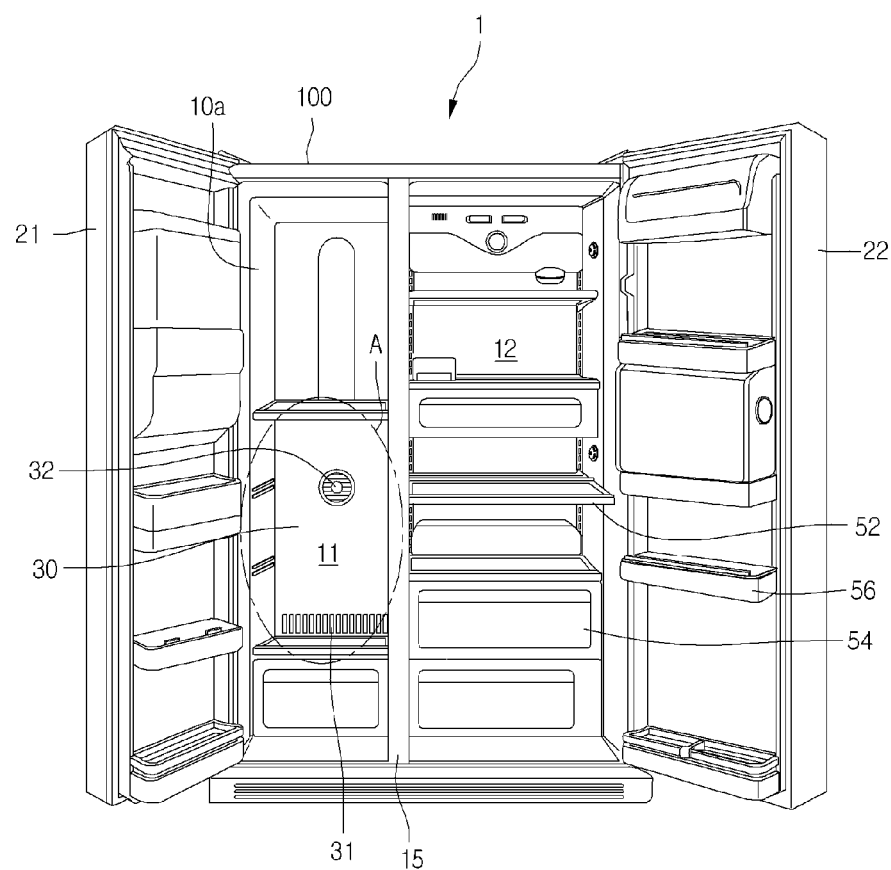
FIG. 1 is a perspective view of a refrigerator according to a first exemplary embodiment of the present invention.
Figure 2:
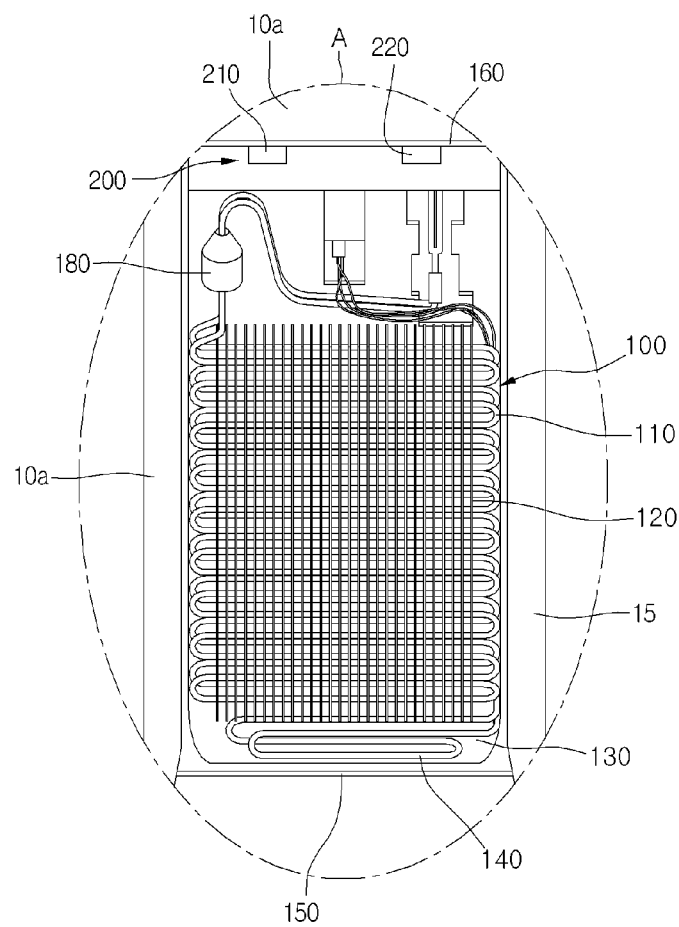
FIG. 2 is a view showing the portion "A" of FIG. 1 with a cover plate removed.
Figure 3:
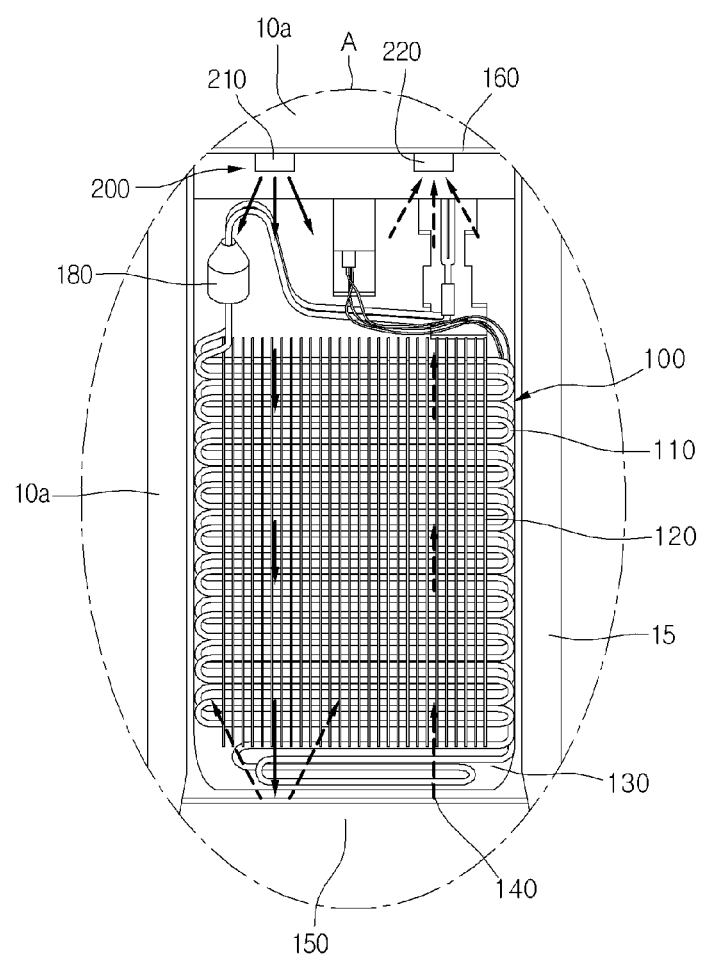
FIG. 3 is a view showing the operations of a soundsource transmitting unit and a soundsource receiving unit according to the first exemplary embodiment of the present invention.

FIG. 1 is a perspective view of a refrigerator according to a first exemplary embodiment of the present invention, FIG. 2 is a view showing the portion "A" of FIG. 1 with a cover plate removed, and FIG. 3 is a view showing the operations of a soundsource transmitting unit and a soundsource receiving unit according to the first exemplary embodiment of the present invention.

Referring to FIGS. 1 to 3, a refrigerator 1 according to the first exemplary embodiment of the present invention includes a main body 10 in which a storage chamber is formed and of which the front is open. A freezing compartment 11 and a cool chamber 12 are included in the storage chamber and they may be separated by a partition 15.

Further, the main body 10 includes an inner case 10a that forms at least one side of the storage chamber. The inner external appearance of the storage chamber may be defined by the inner case 10a.

The refrigerator 1 includes a freezing compartment door 21 and a cool chamber door 22 that are rotatably connected to the front of the main body 10 and selectively close the freezing compartment 11 and the cool chamber 12, respectively.

In the present exemplary embodiment, a side-by-side type having a freezing compartment and a cool chamber at the left and right is exemplified. However, it should be understood that the spirit of the present invention may be applied to a top-mount type in which a freezing compartment is formed at the upper portion and a cool chamber is formed at the lower portion or a bottom-freezer type in which a freezing compartment is formed at the lower portion and a cool chamber is formed at the upper portion.

In detail, the storage chamber includes a shelf 52 where reserves can be received and a storage box 54 that can be drawn. Further, a plurality of door baskets 56 where reserves are received may be provided on the rear sides of the doors 21 and 22.

On the other hand, a cold air exit 32 through which the cold air generated by the evaporator 100 is discharged to the freezing compartment 11 is formed in the freezing compartment 11. The cold air exit 32 is provided at the rear side of the freezing compartment 11 and may be formed through a cover plate 30. Further, the evaporator 100 is disposed behind the cover plate 30.

A cold air inlet 31 through which the cold air that has circulated in the freezing chamber 11 flows into the evaporator 100 is formed at the cover plate 30. The cold air inlet 31 may be formed at the lower portion of the cover plate 30.

The cold air generated by the evaporator 100 is discharged to the freezing compartment 11 through the cold air exit 32 and the cold air that has circulated in the freezing compartment 11 can be moved to the evaporator 100 through the cold air inlet 31 and cooled again.

The evaporator 100 includes a refrigerant pipe 110 through which a refrigerant flows and cooling fins 120 in which the refrigerant pipe 110 is inserted and allows easy heat exchange between the refrigerant and the surrounding air.

The refrigerant that has passed through the refrigerant pipe 110 may flow again to a compressor (not shown) through an accumulator 180.

Further, a heating unit 140 that removes frost on the surface of the evaporator 100 is provided under the evaporator 100. A defrosting heater may be included in the heating unit 140. The heating unit 140 operates with heat exchange stopped in the evaporator 200 and can remove frost by supplying heat to the evaporator 240.

A defrosted water basin 130 where defrosted water generated while defrosting the evaporator 100 collects is provided under the evaporator 100.

Meanwhile, a sensor unit 200 that senses the amount of frost on the evaporator, using transmitted/received soundsources (sound wave or ultrasonic wave), is provided at one side of the evaporator 100. The sensor unit 200 may be referred to as a "frost sensor unit".

The sensor unit 200 includes a soundsource transmitting unit 210 that transmits a predetermined magnitude of volume and a soundsource receiving unit 220 that receives the soundsource transmitted from the soundsource transmitting unit 210 and then reflected from the evaporator 100.

The soundsource transmitting unit 210 may be a sound wave transmitting unit that transmits a sound wave within the audio frequency band or an ultrasonic wave transmitting unit that transmits an ultrasonic wave at the audio frequency band or more.

The soundsource receiving unit 220 may be a microphone that receives a sound wave or an ultrasonic sensor that receives an ultrasonic wave.

The soundsource transmitting unit 210 and the soundsource receiving unit 220 may be mounted on a sensor mounting portion 160. The sensor mounting portion 160 is provided to the inner case 10a and may be disposed above the evaporator 100.

Further, a reflective plate 150 that reflects the soundsource transmitted from the soundsource transmitting unit 210 is provided under the evaporator 100. The reflective plate 150 may be integrally formed with the defrosted water basin 130. However, the reflective plate 150 may be removed and the defrosted water basin 130 may perform the function of the reflective plate.

The operation of the sensor unit will be briefly described.

A sound-source of a predetermined magnitude of volume is transmitted from the soundsource transmitting unit 210. The transmitted soundsource is reflected from the reflective plate 150 or the defrosted water basin 130 through the evaporator 100. Obviously, a portion of the transmitted soundsource may be reflected from the refrigerant pipe 110 or the cooling fins 120 of the evaporator 100.

Further, the reflected soundsource is received by the soundsource receiving unit 220 through the evaporator 100 again.

In this process, the frost on the evaporator 100 may absorb the transmitted soundsource. Therefore, the soundsource absorbed into the frost is not received by the soundsource receiving unit 220.

As a result, the magnitude (volume) of the soundsource received by the soundsource receiving unit 200 may be slightly smaller than the magnitude of the soundsource transmitted from the soundsource transmitting unit 210. Further, it may be determined that the smaller the magnitude of the soundsource received by the sound-source receiving unit 200 is, the more the frost is made on the evaporator 110.

Figure 4:
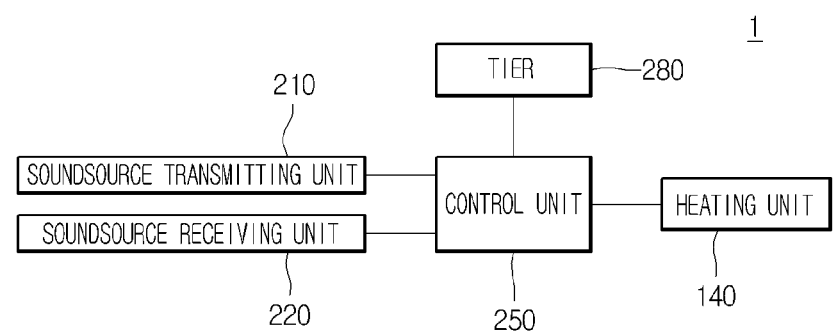
FIG. 4 is a block diagram showing the configuration of the refrigerator according to an exemplary embodiment of the present invention.
Figure 5:
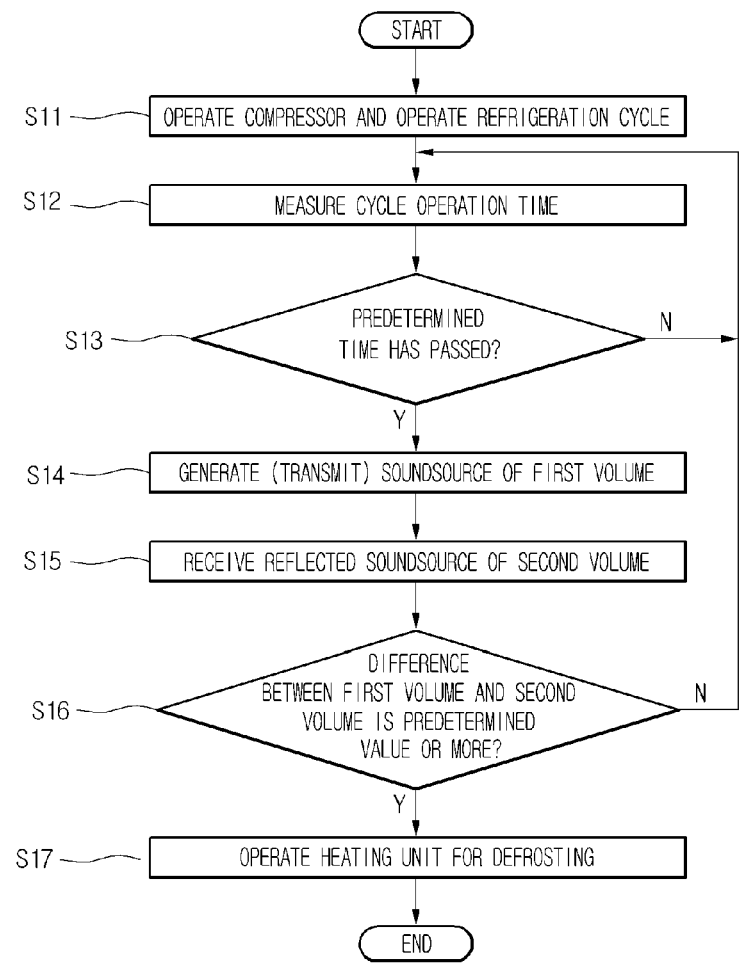
FIG. 5 is a flowchart showing the operation of the refrigerator according to the first exemplary embodiment of the present invention.

FIG. 4 is a block diagram showing the configuration of the refrigerator according to an exemplary embodiment of the present invention and FIG. 5 is a flowchart showing the operation of the refrigerator according to the first exemplary embodiment of the present invention.

Referring to FIGS. 4 and 5, the refrigerator 1 according to the first exemplary embodiment of the present invention includes the soundsource transmitting unit 210 that transmits a sound-source of a predetermined volume to the evaporator 100 and a soundsource receiving unit 220 that receives at least a portion of the soundsource transmitted from the soundsource transmitting unit 210.

Further, the refrigerator 1 includes a timer 280 that shows the point of time of operations of the soundsource transmitting unit 210 and the soundsource receiving unit 220 and a control unit 250 that starts to control the soundsource transmitting unit 210 and the soundsource receiving unit 220 at the time counted by the timer 280.

The timer 280 can count the time that has passed after the refrigeration cycle is operated in the refrigerator 1, for example, after the power of the refrigerator is turned on or the compressor (not shown) is operated.

When the time counted by the timer 280 reaches a predetermined time, the control unit 250 can control the operations of the soundsource transmitting unit 210 and the soundsource receiving unit 220. The predetermined time may have one time value, in which the soundsource transmitting unit 210 and the soundsource receiving unit 220 may operate with a cycle of a predetermined time interval.

The refrigerator 1 includes the heating unit 140 that supply a predetermined amount of heat to remove the frost on the evaporator 100. The control unit may control the operation of the heating unit 140 on the basis of the volume sensed from the soundsource transmitting unit 210 and the soundsource receiving unit 220.

A method of controlling the refrigerator according to the present exemplary embodiment will be described with reference to FIG. 5.

When the power of the refrigerator is turned on or the compressor starts to be operated, the refrigeration cycle in which the refrigerant flows through the compressor, the condenser, the expansion unit, and the evaporator is operated. In this process, the evaporator 100 functions to evaporate the refrigerant that has passed through the expansion unit (S11).

As the refrigeration cycle is operated, the timer 280 measures the operation time of the cycle. Further, it is determined whether the operation time measured by the timer 280 has passed a predetermined time.

The predetermined time may correspond to a time value where frosting can be generated after the refrigeration cycle is operated. That is, the predetermined time may be used as a variable that determines the operational conditions of the sensor unit 200 (S12 and S13).

When the measured operation time has passed the predetermined time, a soundsource with the first volume is generated by the soundsource transmitting unit 210 and transmitted to the evaporator 100. The first volume may be a volume of a predetermined magnitude. However, when the measured operation time did not pass the predetermined time, the process returns to step S12 (S14).

A portion of the soundsource transmitted from the soundsource transmitting unit 210 is absorbed into the frost on the evaporator 100. Further, the other of the soundsource is reflected from the reflective plate 150, the defrosted water basin 130, or the refrigerant pipe 110 and the cooling fins 120, and received by the soundsource receiving unit 220.

The soundsource received by the soundsource receiving unit 220 may be defined to have the magnitude of a second volume. The second volume may be set to be smaller than the first volume, and the larger the amount of the sound-source is absorbed into the frost, the smaller the magnitude of the second volume may be. That is, the amount of frost on the evaporator 100 and the received volume may be in inverse proportion.

In other words, the difference value between the first volume and the second volume may change in proportion to the amount of frost on the evaporator 100.

When the soundsource is received by the soundsource receiving unit 220, whether the difference between the first volume and the second volume is a predetermined value or more is determined (S16).

When the difference between the first volume and the second volume is the predetermined value or more, it is determined that the amount of frost is large, and accordingly, the heating unit 140 is operated and the evaporator can be defrosted. However, when the difference between the first volume and the second volume is smaller than the predetermined value, the process may return to step S12 (S17).

According to the configuration and control method, there is an effect that the actual amount of frost on the evaporator 100 can be sensed in accordance with the operation of the sensor unit 200 and defrosting can be performed in accordance with the sensed amount.

Figure 6:
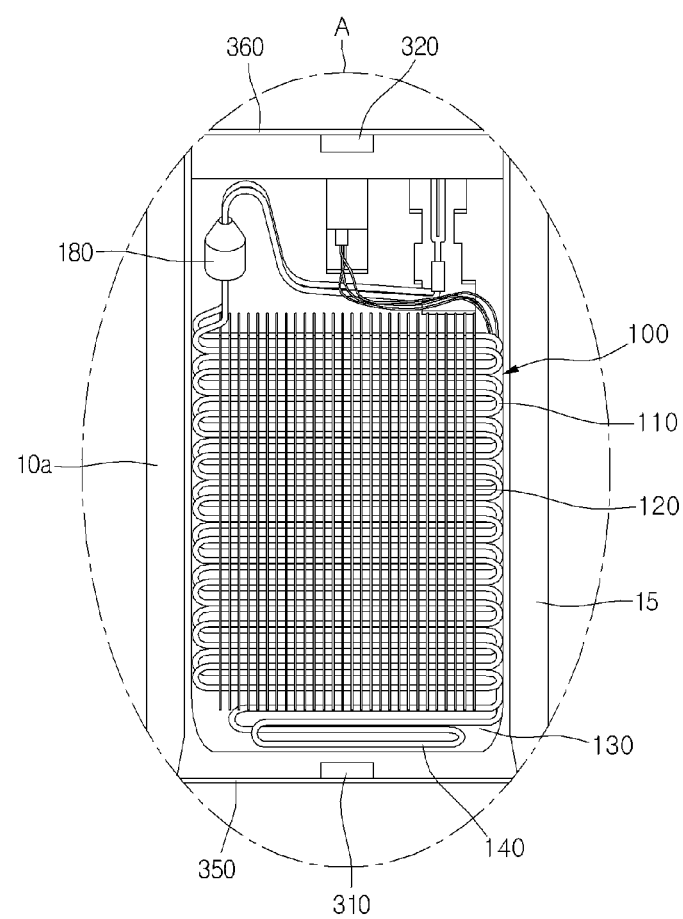
FIG. 6 is a view showing the configuration of a refrigerator according to a second exemplary embodiment of the present invention.

FIG. 6 is a view showing the configuration of a refrigerator according to a second exemplary embodiment.

Referring to FIG. 6, a soundsource transmitting unit 310 according to the second exemplary embodiment is disposed under the evaporator 100 and a soundsource receiving unit 320 is disposed above the evaporator 100. The soundsource transmitting unit 310 is fixed to a first fixing portion 350 and the soundsource receiving unit 320 is fixed to a second fixing portion 360.

The operation of the soundsource transmitting unit 310 and the soundsource receiving unit 320 according to the present exemplary embodiment will be briefly described.

As described in the first exemplary embodiment, when a predetermined condition, that is, the operation time of the refrigeration cycle has passed a predetermined time, a soundsource is transmitted from the soundsource transmitting unit 310. The transmitted soundsource is received by the soundsource receiving unit 320 through the evaporator 100. However, at least a portion of the transmitted soundsource is absorbed into frost on the evaporator 100.

As a result, the magnitude of the soundsource received by the soundsource receiving unit 320 may be smaller than the magnitude of the soundsource transmitted from the soundsource transmitting unit 310, by the magnitude of the soundsource absorbed into the frost.

When the difference in magnitude of the volumes sensed from the soundsource transmitting unit 310 and the soundsource receiving unit 320 is a predetermined value or more, it is determined that the amount of frost on the evaporator is large, and accordingly, the heating unit 140 can operate and perform defrosting.

Figure 7:
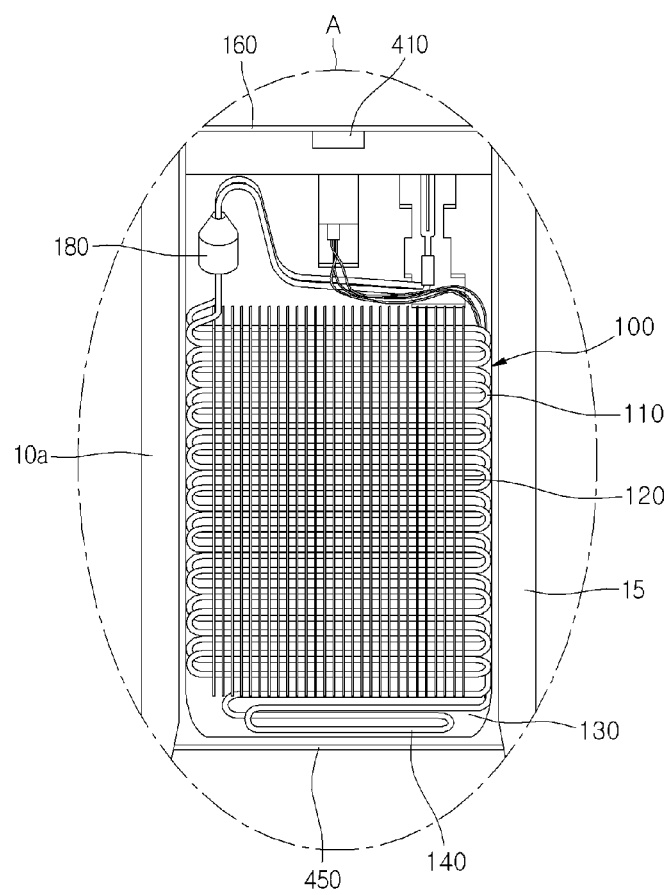
FIG. 7 is a view showing the configuration of a refrigerator according to a third exemplary embodiment of the present invention.

FIG. 7 is a view showing the configuration of a refrigerator according to a third exemplary embodiment of the present invention.

Referring to FIG. 7, a refrigerator 1 according to the third exemplary embodiment of the present invention includes a soundsource transmitting/receiving unit 410 that transmits/receives a soundsource, at one side of the evaporator 100. The soundsource transmitting/receiving unit 410 may be mounted and fixed to the sensor mounting portion 160.

A reflective plate 450 that reflects a soundsource may be proposed opposite the sensor mounting portion 160.

A predetermined soundsource (sound wave or ultrasonic wave) may be transmitted to the soundsource transmitting/receiving unit 410 in response to an order from the control unit 250. In particular, the ultrasonic wave is useful for measuring reverberation, and thus may be applied as the soundsource in the present exemplary embodiment.

A portion of the transmitted soundsource is absorbed into frost on the evaporator and the other of the soundsource is reflected from the reflective plate 450 or the defrosted water basin 130 and then received by the soundsource transmitting/receiving unit 410.

When the difference in volume transmitted and received by the soundsource transmitting/receiving unit 410 is a predetermined value or more, it is determined that the amount of frost on the evaporator 100 is large. In this case, the control unit 250 controls the heating unit 140 to defrost the evaporator 100.

Figure 8:
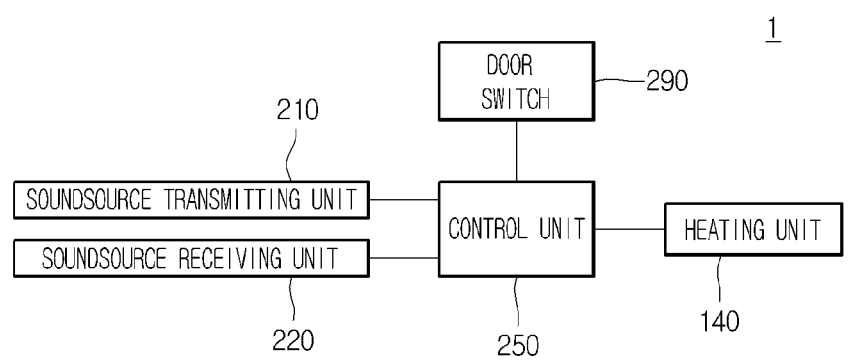
FIG. 8 is a block diagram showing the configuration of a refrigerator according to a fourth exemplary embodiment of the present invention.
Figure 9:
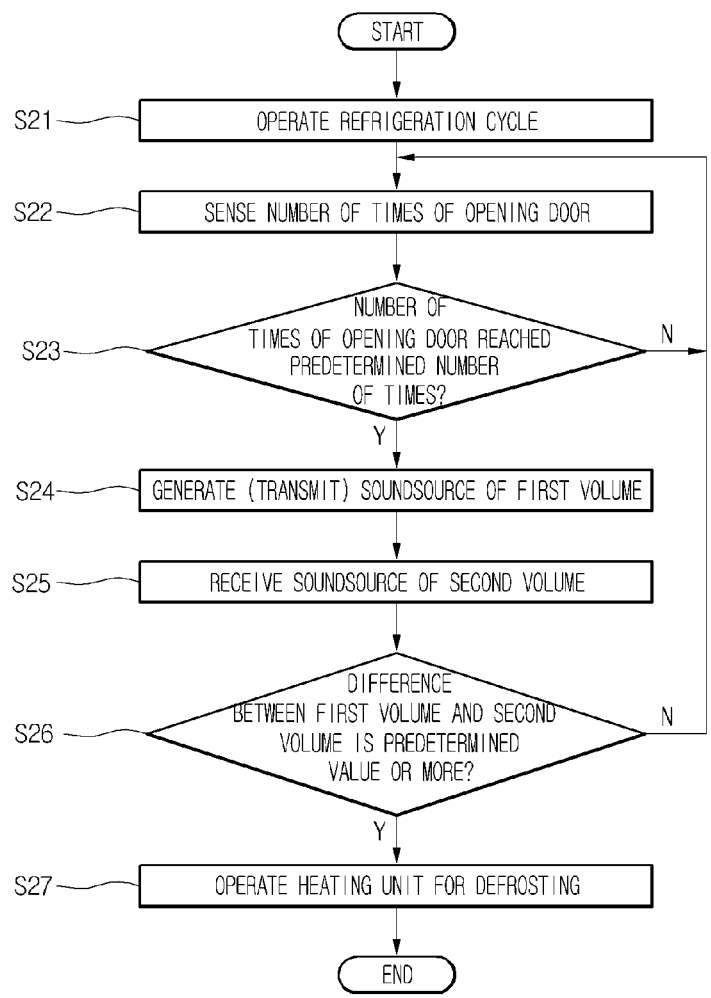
FIG. 9 is a flowchart showing the operation of the refrigerator according to the fourth exemplary embodiment.

FIG. 8 is a block diagram showing the configuration of a refrigerator according to a fourth exemplary embodiment of the present invention and FIG. 9 is a flowchart showing the operation of the refrigerator according to the fourth exemplary embodiment.

Referring to FIG. 8, a refrigerator 1 according to the fourth exemplary embodiment of the present invention includes a soundsource transmitting unit 210 that transmits a soundsource, a soundsource receiving unit 220 that receives the transmitted soundsource that reflects from or passes through a predetermined portion, a heating unit 140 that generates heat to defrost the evaporator 100, a door switch 290 that senses whether the doors 21 and 22 are opened, and a control unit 250 that controls these components.

A method of controlling the refrigerator according to the present exemplary embodiment will be described with reference to FIG. 9.

While the refrigeration cycle is operated after the power of the refrigerator is turned on, the number of times of opening the doors 21 and 22 can be sensed by the door switch 290.

When the doors 21 and 22 are frequently opened, wet air with predetermined humidity flows into the storage chambers 11 and 12 and the inflow wet air is likely to become frost on the evaporator 100 under a low-temperature environment (S21 and S22).

When the number of times of opening the doors 21 and 22 reaches a predetermined number of times, the soundsource transmitting unit 210 transmits a sound-source of a first volume. The transmitted soundsource reflects or passes around the evaporator 100 and is received by the soundsource receiving unit 220.

That is, the soundsource transmitting unit 210 and the soundsource receiving unit 220 may be operated in accordance with whether a predetermined condition, that is, the number of times of opening the doors 21 and 22 reaches a predetermined number of times. In other words, the "number of times of opening the doors" may be used as a variable that determines the operational condition of the sensor unit 200.

On the contrary, when the number of times of opening the doors 21 and 22 does not reach the predetermined number of times, the process returns to step S22.

In this process, the volume received by the soundsource receiving unit 220 may be defined as a second volume. A portion of the soundsource received by the soundsource receiving unit 210 is absorbed into the frost on the evaporator 100, and thus may not be received by the sound-source receiving unit 220. As a result, the second volume may have a value smaller than the first volume (S23, S24, and S25).

Whether the difference between the first volume and the second volume is a predetermined value is determined. When the difference is the predetermined value or more, the heating unit 140 is operated to remove the frost on the evaporator 100, thereby defrosting the evaporator. However, when the difference is smaller than the predetermined value, the process may return to step S22 (S26 and S27).

Other exemplary embodiments will be proposed.

In the present exemplary embodiment, although the operations of the soundsource transmitting unit 210 and the soundsource receiving unit 220 are controlled in accordance with the number of times of opening the doors 21 and 22 by using the door switch 290, unlikely, the operations may be controlled in accordance with the open time of the doors 21 and 22.

That is, a "door open time" may be used as a variable that determines the operational condition of the sensor unit 200.

When the open time of the doors 21 and 22 has passed a predetermined time, the volumes transmitted/received by the operations of the soundsource transmitting unit 210 and the soundsource receiving unit 220 can be sensed. Further, the amount of frost on the evaporator 100 may be determined and the operation of the heating unit 140 may be controlled in accordance with the sensed volume.

Figure 10:
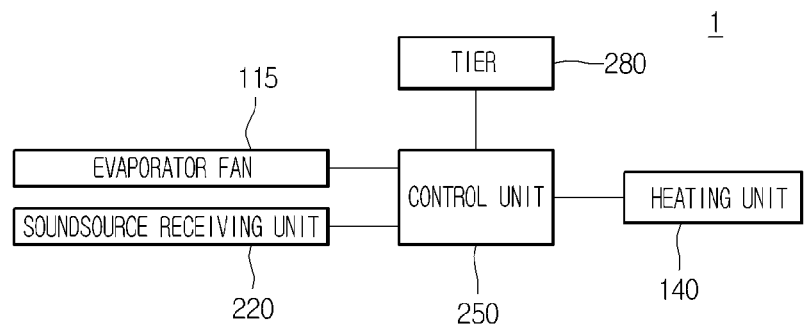
FIG. 10 is a block diagram showing the configuration of a refrigerator according to a fifth exemplary embodiment of the present invention.

FIG. 10 is a block diagram showing the configuration of a refrigerator according to a fifth exemplary embodiment of the present invention.

Referring to FIG. 10, a refrigerator 1 according to the fifth exemplary embodiment of the present invention includes an evaporator fan 115 that generates a predetermined volume, a soundsource receiving unit that receives the soundsource that is transmitted from the evaporator fan 115 and reflects or passes around the evaporator 100, a timer for determining the operation time of the soundsource receiving unit 220, a heating unit 140 that defrosts the evaporator 100, and a control unit 250 that controls these components.

The evaporation fan 115 is disposed at one side of the evaporator 100 and discharges the cold air generated from the evaporator 100 to the storage chamber. The magnitude of the sound generated by the evaporator fan 115 may be stored in advance in the control unit 250.

When the operation time of the refrigeration cycle has passed a predetermined time, the control unit 250 controls the soundsource receiving unit 220 and the magnitude of the received soundsource can be sensed.

Further, when the magnitude of the sound of the evaporator fan 115 and the volume of the soundsource receiving unit 220 are a predetermined magnitude or more, it is determined that the amount of frost on the evaporator 100 is large and the heating unit 150 can operate and defrost the evaporator.

According to this configuration, it is possible to sense the volume by using the evaporator fan without a specific soundsource receiving unit, and accordingly, there is an effect that the manufacturing cost can be reduced.

A sixth exemplary embodiment of the present invention will be described hereafter. Comparing the present exemplary embodiment with the exemplary embodiments described above, there is a difference only in the configuration for determining the amount of frost on the evaporator; therefore, the difference is mainly described and the description and reference numerals of the exemplary embodiments described above are used for the same configurations.

Figure 11:
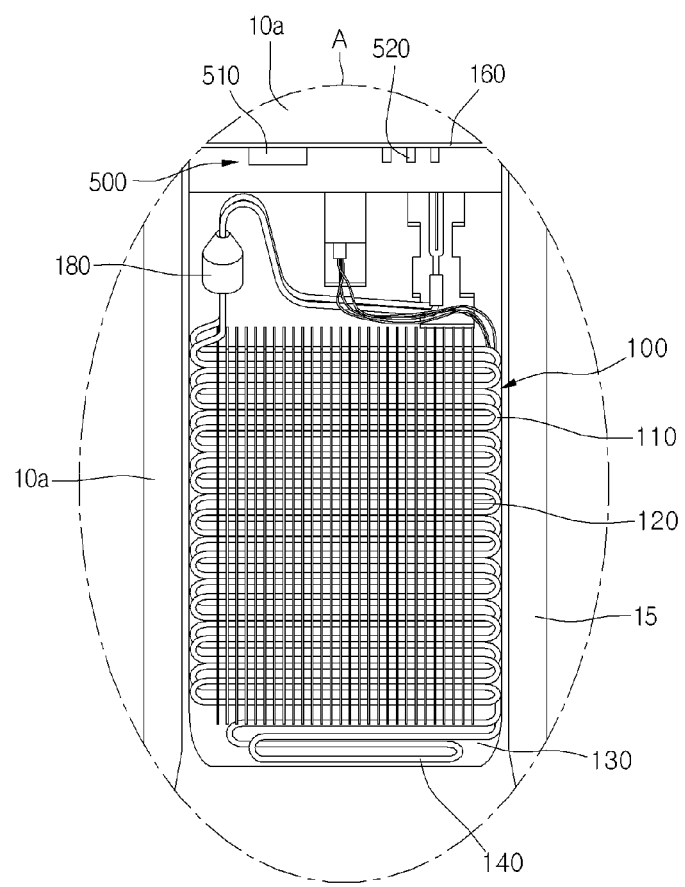
FIG. 11 is a view showing the portion "A" of FIG. 1 with the cover plate removed, as a sixth exemplary embodiment of the present invention.

FIG. 11 is a view showing the portion "A" of FIG. 1 with the cover plate removed, as a sixth exemplary embodiment of the present invention.

Referring to FIG. 11, a photographing device 500 that photographs an evaporator 100 according to the sixth exemplary embodiment of the present invention to sense the amount of frost on the evaporator is provided at one side of the evaporator 100. The photographing device 500 may be referred to as a "frost sensor unit".

In detail, the photographing device 500 includes a photographing unit 510 that take an image of the evaporator 100, that is, a shape of frost on a refrigerant pipe 110 and cooling fins 120 that constitute the evaporator 100 and the evaporator 100, and a lighting unit 520 that is provided at one side of the photographing unit 510 and emits light to the evaporator 100.

A heater (not shown) may be provided around a lens (not shown) or the lighting unit 520 provided in the photographing unit 510. The photographing unit 510 and the lighting unit 520 may be exposed to a low-temperature environment and frosted, thus the heater may prevent frosting by operating periodically or at a predetermined time.

The lighting unit 520 includes an LED. The lighting unit 520 is turned on when the photographing unit 510 takes a picture, and may keep off when the photographing unit 510 does not take a picture.

Although it is described in the present exemplary embodiment that the photographing unit 510 and the lighting unit 520 are separately configured, unlikely, the lighting unit 520 may be integrally formed with the photographing unit 510. That is, the lighting unit 520 may be provided at the photographing unit 510 to simultaneously on-operate when the photographing unit 510 takes a picture.

Figure 12:
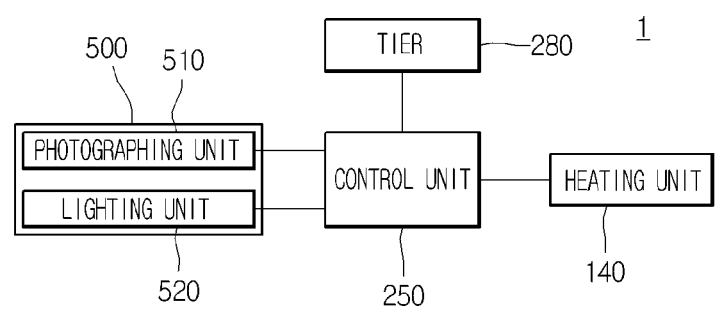
FIG. 12 is a block diagram showing the configuration of a refrigerator according to the sixth exemplary embodiment of the present invention.
Figure 13:
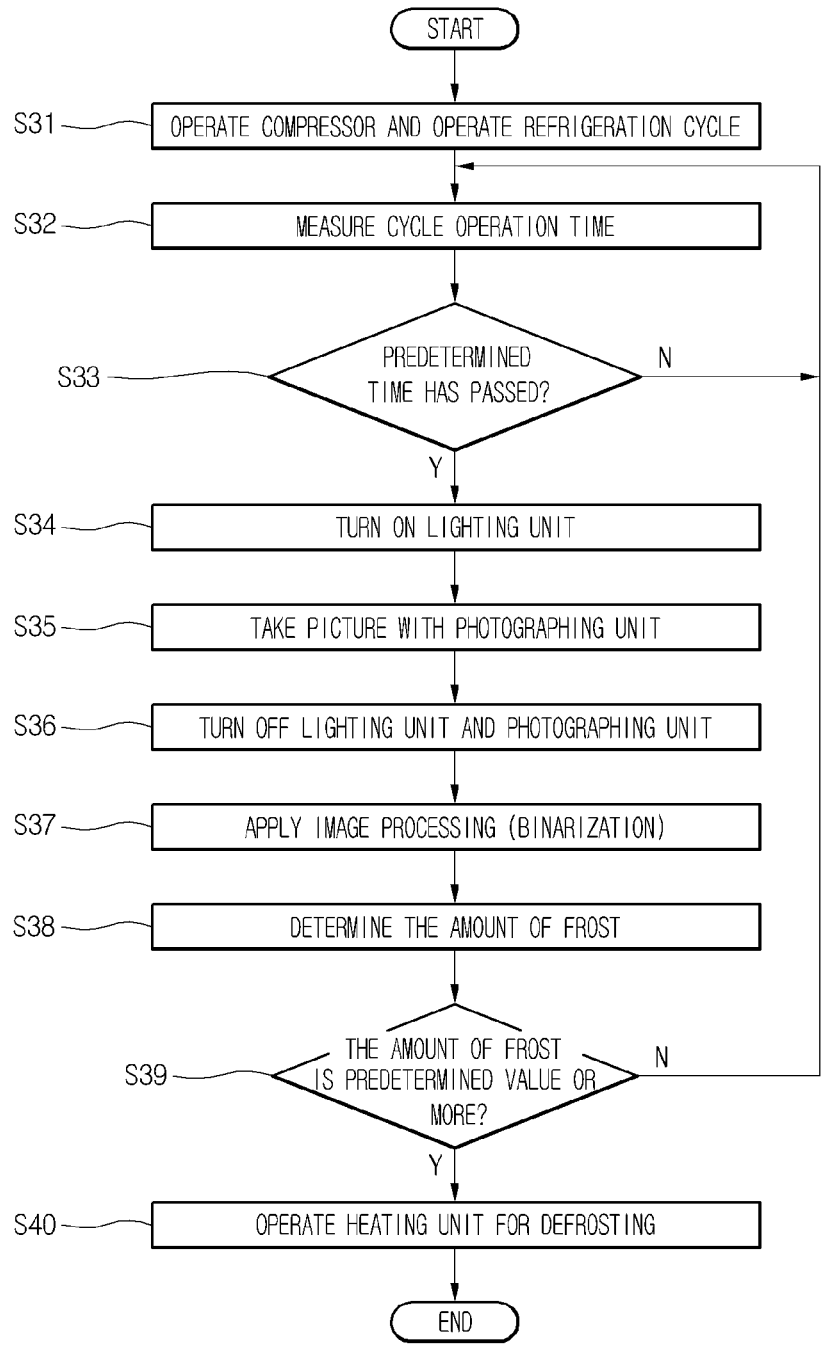
FIG. 13 is a flowchart showing the operation of the refrigerator according to the sixth exemplary embodiment of the present invention.

FIG. 12 is a block diagram showing the configuration of a refrigerator according to the sixth exemplary embodiment of the present invention and FIG. 13 is a flowchart showing the operation of the refrigerator according to the sixth exemplary embodiment of the present invention.

Referring to FIGS. 12 and 13, a refrigerator 1 according to a sixth exemplary embodiment of the present invention includes the photographing unit 510 and the lighting unit 520 for photographing the evaporator 100, a timer 280 that determines the operation time of the photographing unit 510 and the lighting unit 520, a heating unit 140 that generates heat to defrost the evaporator 100, and a control unit 250 that controls these components.

The timer 280 can count the time that has passed after the refrigeration cycle is operated in the refrigerator 1, for example, after the power of the refrigerator is turned on or the compressor (not shown) is operated.

When the time counted by the timer 280 reaches a predetermined time, the control unit 250 can control the operations of the photographing unit 510 and the lighting unit 520. The predetermined time may have one time value, in which the photographing unit 510 and the lighting unit 520 may operate with a cycle of a predetermined time interval.

As described above, since the photographing unit 510 and the lighting unit 520 are selectively operated in accordance with a predetermined condition (time), there is an advantage in that the power consumption can be reduced.

When it is determined that a predetermined amount of or more frost is generated, from the image taken by the photographing unit 510, the control unit 250 operates the heating unit 140 and the frost on the evaporator 100 can be melted and removed.

The process of determining the amount of frost from an image taken by the photographing unit 510 will be described hereafter.

The original image taken by operating the photographing unit 510 includes frost (object) on the evaporator 100 and the background around the frost. The background may include the image of the refrigerant pipe 110 and the cooling fins 120 that constitute the evaporator 100, or the image around the evaporator 100.

The frost may have a higher brightness value, that is a light color, than the background. An image processing method that acquires a pixel value that is proportion to the amount of frost on the evaporator 100, particularly, binarization may be applied in order to separate the frost from the background.

The "binarization" means a work of changing (binarizing) the pixels to 0 and 1 (or 255) in accordance with the brightness value of the image. The object in the image can be separated from the background by the binarization.

In this exemplary embodiment, the object may correspond to the frost and the background may correspond to the image around the frost.

A critical value to be a reference is defined to separate the frost from the background. The pixels of a brightness value higher than the critical value are recognized as 255 and the pixels of a brightness value lower than the critical value are recognized as 0.

For example, when a pixel in an image taken by the photographing unit 510 has brightness of 150 and the critical value is set to 120, the pixel is recognized as 255 and can be determined as frost.

On the contrary, when another pixel has brightness of 110 and the critical value is set to 120, the pixel is recognized as 0 and can be determined as the background. For the convenience of description, the pixel corresponding to 255 are referred to as a "bright pixel" and the pixel corresponding to 0 is referred to as a "dark pixel" hereafter.

The critical value may be set as an appropriate value in consideration of the brightness of the background of the evaporator 100 and the frost. Further, the critical value may be set and stored in advance in the control unit 250.

Further, the binarization is programmed and stored in the control unit 250 and the control unit 250 divides the image taken by the photographing unit 510 into bright pixels and dark pixels by applying binarization. The bright pixels correspond to frost and the dark pixels correspond to the portion corresponding to the background.

Since the pixel values corresponding to frosting on the evaporator 100 are in proportion to the amount of frost on the evaporator 100, when it is sensed that the number of bright pixels is a predetermined number or more, it may be possible to determine that a predetermined amount of or more frost is on the evaporator 100.

The control unit may control the heating unit 140 to perform defrosting.

A method of controlling the refrigerator 1 according to the present exemplary embodiment is described with reference to FIG. 13.

When the power of the refrigerator is turned on or the compressor starts to operate, the refrigeration cycle is operated while the refrigerant flows through the compressor, the condenser, the expansion unit, and the evaporator. The evaporator 100 functions to evaporate the refrigerant that has passed through the expansion unit (S31).

As the refrigeration cycle is operated, the timer 280 measures the operation time of the cycle. Further, it is determined that whether the operation time measured by the timer 280 has passed a predetermined time (S32 and S33).

When the measured operation time has passed the predetermined time, the lighting unit 520 is turned on and the photographing unit 510 operates and photographs the frost on the evaporator 100 and the surrounding background. However, when the measured operation time did not pass the predetermined time, the process returns to step S32 (S34 and S35).

Further, when the photographing unit 510 finishes photographing, the power of the photographing unit 510 and the lighting unit 520 is turned off. There is an advantage in that unnecessary consumption of power can be prevented by the control (S36).

Binarization is applied to the image taken by the photographing unit 510. When binarization is applied to the image, the frost on the evaporator 100 is defined by bright pixels and the background around the frost is defined by dark pixels. The amount of frost on the evaporator 100 can be determined in accordance with the number of the bright pixels (S37 and S38).

When it is determined that the number of the bright pixels is larger than a predetermined number of pixels, that is, when it is determined that the amount of frost on the evaporator 100 is larger than a predetermined value (amount), the heating unit 140 operates and the evaporator can be defrosted. However, when it is determined that the amount of frost on the evaporator 100 is smaller than the predetermined value (amount), the process may return to step S32 (S39 and S40).

According to these configuration and control method, there is an effect that the actual amount of frost on the evaporator 100 can be sensed by the operation of the photographing device 500 and defrosting can be performed in accordance with the sensed amount.

Figure 14:
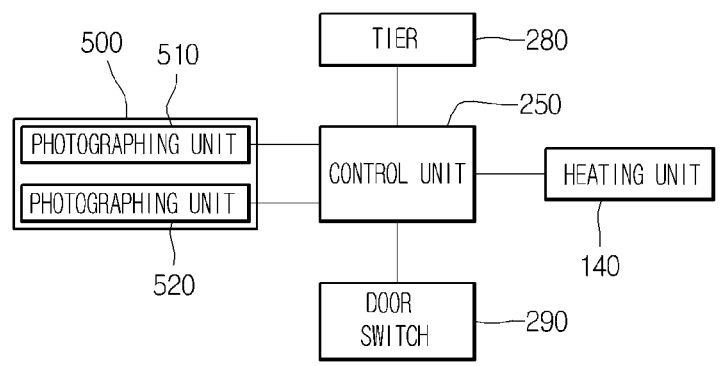
FIG. 14 is a block diagram showing the configuration of a refrigerator according to a seventh exemplary embodiment of the present invention.
Figure 15:
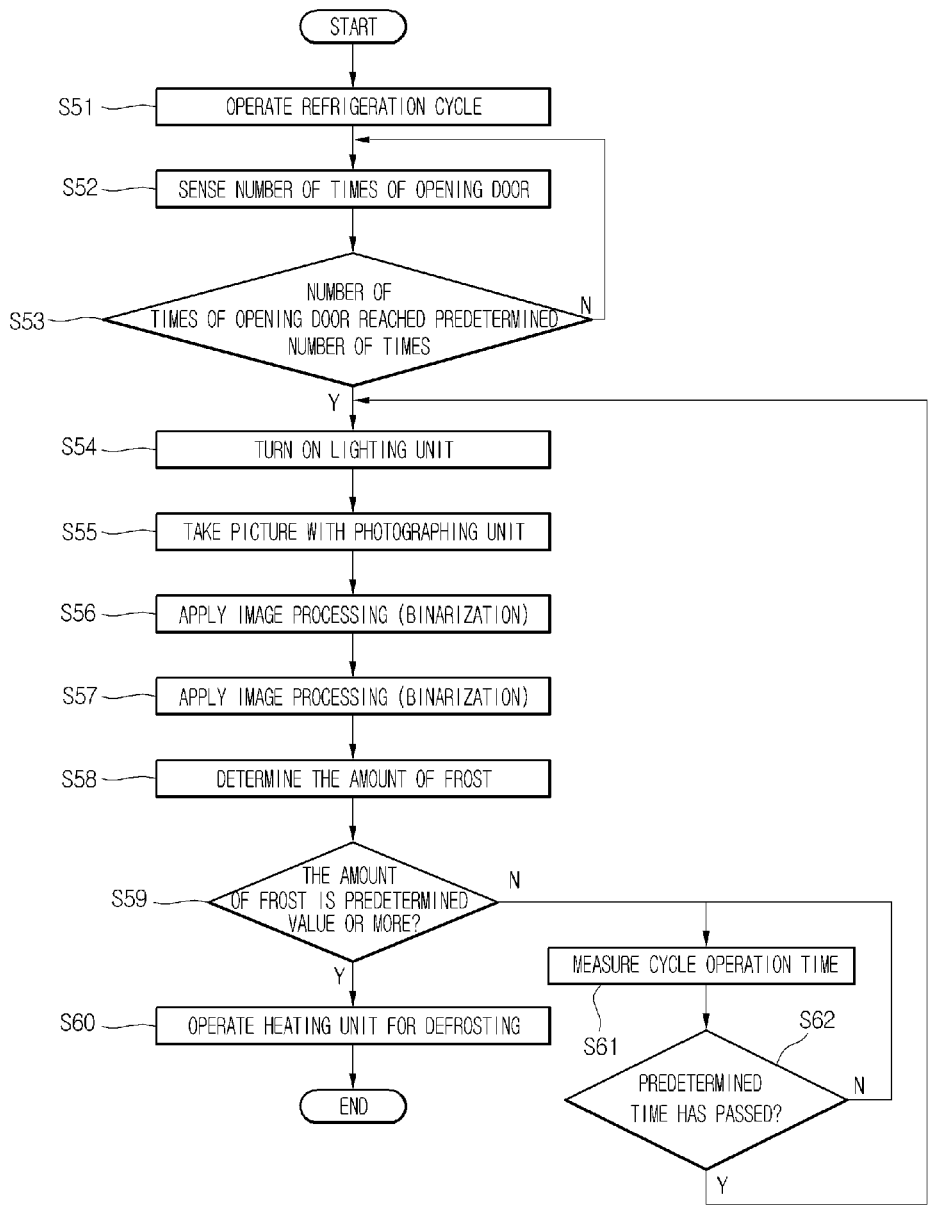
FIG. 15 is a flowchart showing the operation of the refrigerator according to a seventh exemplary embodiment of the present invention.

FIG. 14 is a block diagram showing the configuration of a refrigerator according to a seventh exemplary embodiment of the present invention and FIG. 15 is a flowchart showing the operation of the refrigerator according to a seventh exemplary embodiment of the present invention.

Referring to FIGS. 14 and 15, a refrigerator 1 according to the seventh exemplary embodiment includes a photographing unit 510 that takes a picture, a lighting unit 520 that lights the evaporator 100 such that the photographing unit 510 can easily take a picture, and a heating unit 140 that generates heat to defrost the evaporator 100.

Further, the refrigerator 1 further includes a timer 280 that counts the operation time of the photographing unit 510 and the lighting unit 520, a door switch 290 that senses whether the doors 21 and 22 are opened, and a control unit 250 that controls these components.

A method of controlling the refrigerator according to the present exemplary embodiment will be described with reference to FIG. 15.

While the refrigeration cycle is operated after the power of the refrigerator is turned on, the number of times of opening the doors 21 and 22 can be sensed by the door switch 290.

When the doors 21 and 22 are frequently opened, wet air with predetermined humidity flows into the storage chambers 11 and 12 and the inflow wet air is likely to become frost on the evaporator 100 under a low-temperature environment (S51 and S52).

When the number of times of opening the doors 21 and 22 reaches a predetermined number of times, the lighting unit 520 is turned on and the photographing unit 510 operates to photograph frost on the evaporator 100 and the surrounding background. That is, the photographing unit 510 and the lighting unit 520 may be operated in accordance with whether a predetermined condition, that is, the number of times of opening the doors 21 and 22 reaches a predetermined number of times.

On the contrary, when the number of times of opening the doors 21 and 22 does not reach the predetermined number of times, the process returns to step S52 (S53, S54, and S55).

Further, when the photographing unit 510 finishes photographing, the power of the photographing unit 510 and the lighting unit 520 is turned off. There is an advantage in that unnecessary consumption of power can be prevented by the control (S56).

The amount of frost on the evaporator 100 is determined by applying binarization to the image taken by the photographing unit 510 (S57 and S58).

When it is determined that the amount of frost on the evaporator 100 is a predetermined value (amount) or more, the heating unit 140 operates and defrosts the evaporator (S59 and S60).

However, when it is determined that the amount of frost on the evaporator 100 is smaller than a predetermined value (amount), the operation time of the following refrigeration cycle is measured by the timer 280 (S61).

When the time measured by the timer 280 has passed a predetermined time, the process returns to step S54 and the photographing unit 510 and the lighting unit 520 operate (S62). Further, step S24 to step S30 are performed again.

On the contrary, when the time measured by the timer 280 did not pass the predetermined time, step S61 is performed.

Another exemplary embodiment will be proposed.

Although the operations of the photographing unit 510 and the lighting unit 520 are controlled in accordance with the number of times of opening the doors 21 and 22 by using the door switch 290 in the present exemplary embodiment, unlikely, the operations may be controlled in accordance with the open time of the doors 21 and 22.

That is, when the open time of the doors 21 and 22 has passed a predetermined time, the photographing unit 510 and the lighting unit 520 operate and the image of the frost on the evaporator 100 and the background can be acquired. Further, it is possible to determine the amount of frost on the evaporator 100 from the acquired image and to control the operation of the heating unit 140.

According to a refrigerator of the present invention, it is possible to determine the amount of frost on the evaporator by using a frost sensor unit, thereby achieving remarkable industrial applicability.

According to a refrigerator of an exemplary embodiment of the present invention, it is possible to easily determine the amount of frost on the evaporator in accordance with the difference between the volume transmitted from the sound-source transmitting unit and the volume received by the sound-source receiving unit, and to effectively defrost the evaporator in accordance with the determined amount of frost.

Further, since the sound-source transmitting unit and the sound-source receiving unit operate in accordance with predetermined conditions and the actual amount of frost can be determined by the sound-source transmitting unit and the sound-source receiving unit, it is possible to prevent unnecessary defrosting.

Further, it is possible to effectively sense the volume absorbed into the frost on the evaporator and the amount reflected from (passing through) the evaporator, in accordance with the arrangement of the sound-source transmitting unit and the sound-source receiving unit.

Further, since the heating unit can be operated only at the point of time where defrosting is needed in accordance with the sensed result of the sound-source transmitting unit and the sound-source receiving unit, it is possible to reduce the power consumption.

Further, it is possible to photograph the frost on the evaporator with the photographing device and to determine the amount of frost on the basis of the taken picture.

Further, it is possible to divide the frost and the background from the image taken by the photographing device by using an image processing method, particularly binarization, and to accurately determine the actual amount of frost in accordance with the number of pixels brighter than a reference value.

Further, since defrosting can be selectively performed in accordance with the actual amount of frost, it is possible to prevent unnecessary defrosting and reduce the power consumption.

What is claimed is:

1. A refrigerator, comprising:
a compressor, a condenser, and an expansion unit;
an evaporator for evaporating a refrigerant that has passed through the expansion unit;
a heating unit for providing heat for defrosting the evaporator;
a photographing device provided at one side of the evaporator and disposed to photograph the evaporator, so as to sense the amount of frost on the evaporator, the photographing device including a photographing unit for photographing frost on the evaporator and the surrounding background; and
a control unit configured to determine the amount of frost on the evaporator from an image taken by the photographing device by acquiring pixel values which are proportionate to amount of frost on the evaporator by applying image processing which includes binarization that separates the frost from other acquired images to determine the amount of frost on the evaporator, the control unit further configured to control the heating unit to operate when the determined amount of frost exceeds a predetermined amount.

2. The refrigerator of claim 1, wherein the photographing device further includes a lighting unit that emits light to the evaporator when the photographing unit takes a picture.

3. The refrigerator of claim 1, wherein the operating conditions of the photographing unit are based on whether an operating time has passed a predetermined time.

4. The refrigerator of claim 1, further comprising:
a storage chamber where cold air is supplied; and
a door disposed to selectively close the storage chamber,
wherein the operating conditions of the photographing unit are based on whether the number of times of opening the door is greater than or equal to a predetermined number or whether the open time of the door has exceeded a predetermined time.

5. The refrigerator of claim 1, wherein the control unit is configured to determine that a pixel having a brightness value higher than a critical value in the acquired image is a first pixel and a pixel having a brightness value lower than the critical value is a second pixel.

6. The refrigerator of claim 5, wherein the control unit is configured to determine that the first pixel in the acquired image indicates frost and the second pixel in the acquired image indicates other elements.

7. The refrigerator of claim 6, wherein the control unit is configured to determine whether a predetermined amount or more of frost is on the evaporator if the number of first pixels in the acquired image is greater than or equal to a predetermined number.

* * * * *